USO08638982B2

(12) United States Patent
Shin et al.

(10) Patent No.: US 8,638,982 B2
(45) Date of Patent: Jan. 28, 2014

(54) METHOD OF TRACKING EYEBALL IN EYEBALL TUMOR TREATMENT

(75) Inventors: Dong Ho Shin, Goyang-si (KR); Sung Yong Park, Goyang-si (KR); Se Byeong Lee, Goyang-si (KR); Myong Geun Yoon, Goyang-si (KR); Young Kyung Lim, Goyang-si (KR); Kwan Ho Cho, Goyang-si (KR)

(73) Assignee: National Cancer Center, Goyang-Si, Gyeonggi-Do (KR)

( * ) Notice: Subject to any disclaimer, the term of this patent is extended or adjusted under 35 U.S.C. 154(b) by 795 days.

(21) Appl. No.: 12/423,206

(22) Filed: Apr. 14, 2009

(65) Prior Publication Data
US 2009/0257639 A1 Oct. 15, 2009

(30) Foreign Application Priority Data
Apr. 14, 2008 (KR) ........................ 10-2008-0034405

(51) Int. Cl.
*G06K 9/00* (2006.01)
(52) U.S. Cl.
USPC ........... 382/103; 382/107; 382/117; 382/132; 351/208
(58) Field of Classification Search
USPC .................. 382/103, 107, 117, 132; 351/208
See application file for complete search history.

(56) References Cited

U.S. PATENT DOCUMENTS

| 6,385,482 | B1 * | 5/2002 | Boksberger et al. ........... 600/424 |
| 7,044,602 | B2 * | 5/2006 | Chernyak ....................... 351/208 |
| 2002/0173778 | A1 * | 11/2002 | Knopp et al. ..................... 606/5 |

FOREIGN PATENT DOCUMENTS

| JP | 10-015087 H | 1/1998 |
| JP | 1019233 A | 7/1998 |
| JP | 11-009708 | 1/1999 |
| JP | 2003-517354 | 5/2003 |
| JP | 2004-129978 | 4/2004 |
| JP | 2004-351152 | 12/2004 |

OTHER PUBLICATIONS

English Abstract; JP Patent Publication No. JP1019233 (A); Published: Jul. 28, 1998; Applicant: Sumiya Toshibumi, et al.; Application No. JP19960359005; Filed: Dec. 27, 1996; Title: Opthalmic Operation Device; (1 pg.).

* cited by examiner

*Primary Examiner* — Brian Q Le
*Assistant Examiner* — Michael Vanchy, Jr.
(74) *Attorney, Agent, or Firm* — Tanya A. Arenson; Casimir Jones, S.C.

(57) ABSTRACT

Disclosed herein is a method of tracking the movement of an eyeball in eyeball tumor treatment. The method includes a calibration step of storing an actual length for each pixel of an image in a storage unit, a template image generation step of storing a patient's eyeball image as a template image of the patient's eyeball in the storage unit, an eyeball location tracking step of, during the treatment of the patient's eyeball, determining whether movement of the treatment image has occurred by comparing treatment images of the patient's eyeball in real time with the template image, and a control step of stopping the operation of the proton beam output device if the movement of the treatment image deviates from a preset tolerance range, and keeping operation of the proton beam output device normal if the movement of the treatment image is within the tolerance range.

5 Claims, 11 Drawing Sheets much the eyeball moves, more particularly for preventing a critical side effect from occurring due to the radiation of a proton beam to an unintended location.

METHOD OF TRACKING EYEBALL IN EYEBALL TUMOR TREATMENT

BACKGROUND OF THE INVENTION

1. Field of the Invention

The present invention relates, in general, to a method of tracking the movement of the eyeball, and, more particularly, to a method of tracking the movement of the eyeball in eyeball tumor treatment.

2. Description of the Related Art

Recently, a method using radiation is widely used as a method of treating tumors such as a cancer. Such a tumor treatment method using radiation is also used as a method of treating the tumor of the eyeball. Meanwhile, recently, a method of treating the tumor of the eyeball using a proton beam has been developed and used.

FIG. 1 is a graph illustrating the characteristics of a proton beam and X-rays, and shows the transmission characteristics of a proton beam and X-rays in a human body.

A proton beam treatment is a kind of radiation treatment.

That is, radiation treatment is configured to destroy cancer cells by radiating X-rays or an electron beam (or a proton beam) onto a human body. However, X-rays that have been widely used in patient treatment up to now have a problem in that it is difficult to avoid a side effect because they damage all tissues along the path thereof, as shown in FIG. 1.

However, a proton beam emits almost all energy immediately before stopping in a human body and becomes extinguished, unlike X-rays. This is a unique phenomenon that appears in a proton beam. A point at which energy is concentrically emitted is referred to as a 'Bragg peak'. That is, the side effect can be reduced because radiation does not reach normal tissues located behind the Bragg peak, and the point of generation of the peak may vary with the intensity of the beam and the material through which the beam passes. Accordingly, when the intensity of the proton beam to be transmitted through a human body is adjusted, it is possible to accurately aim only at cancer cells and destroy them, so that it can be considered that the treatment method using a proton beam is superior to the treatment method using X-rays.

However, although the eyeball tumor treatment using a proton beam has many advantages compared to treatment using general photon rays as described above, there is a problem in that the advantages may be disadvantages at the same time.

That is, the method of treating a tumor using a proton beam can maximize the treatment effect because it is possible to adjust a treatment range to a desired depth and thickness, but a side effect may occur due to the excessive radiation of a proton beam onto normal human body tissues when a patient's treatment location varies during proton beam treatment. In particular, in the case of the eyeball, there is a problem in that a critical side effect may occur.

SUMMARY OF THE INVENTION

Accordingly, the present invention has been made keeping in mind the above problems occurring in the prior art, and an object of the present invention is to provide a method of tracking the movement of the eyeball in eyeball tumor treatment that is capable of blocking the output of a proton beam when the value of the movement of the eyeball exceeds a preset tolerance value during eyeball tumor treatment using the proton beam.

In order to accomplish the above object, the present invention provides a method of tracking the movement of an eyeball in eyeball tumor treatment, the method being applied to an eyeball tumor treatment system, the method including a calibration step of the control unit of the control device of the eyeball tumor treatment system storing an actual length for each pixel of an image, output through an output unit of the control device, in the storage unit of the control device; a template image generation step of the control unit storing a patient's eyeball image, transmitted from the detection device of the eyeball tumor treatment system, as a template image of the patient's eyeball in the storage unit; an eyeball location tracking step of, during the treatment of the patient's eyeball using the proton beam output device of the eyeball tumor treatment system, the control unit determining whether the movement of the treatment image has occurred by comparing treatment images of the patient's eyeball received from the detection device in real time with the template image; and a control step of the control unit stopping the operation of the proton beam output device if, as a result of the determination, the movement of the treatment image is determined to deviate from a preset tolerance range, and keeping operation of the proton beam output device normal if, as a result of the determination, the movement of the treatment image is determined to be within the tolerance range.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
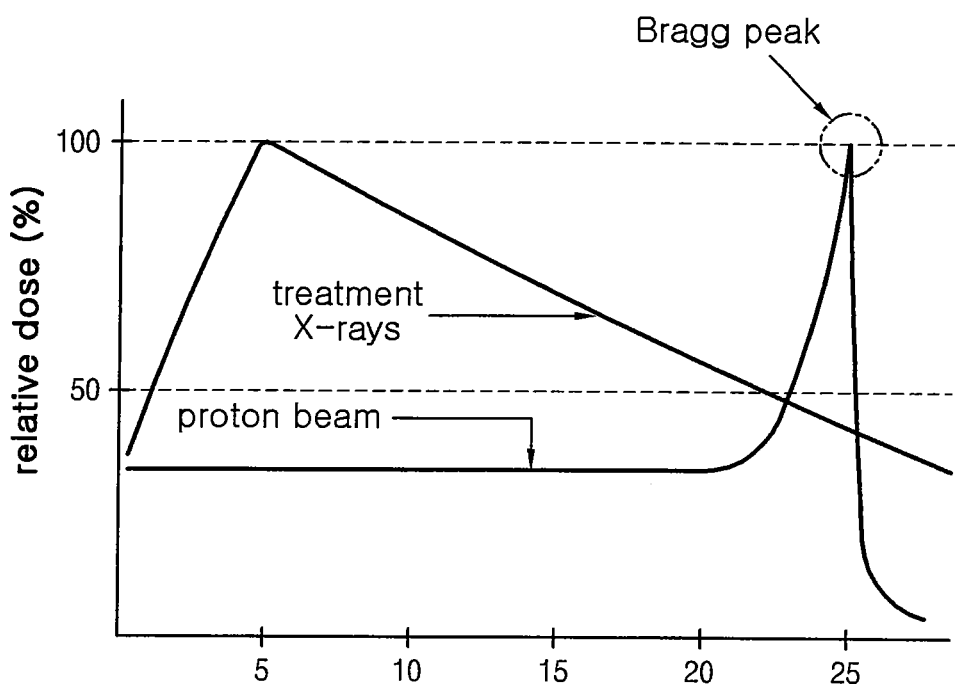
FIG. 1 is a graph illustrating the characteristics of a proton beam and X-rays.

Reference now should be made to the drawings, in which the same reference numerals are used throughout the different drawings to designate the same or similar components.

The present invention will be described in detail below with reference to the accompanying drawings.

Figure 2:
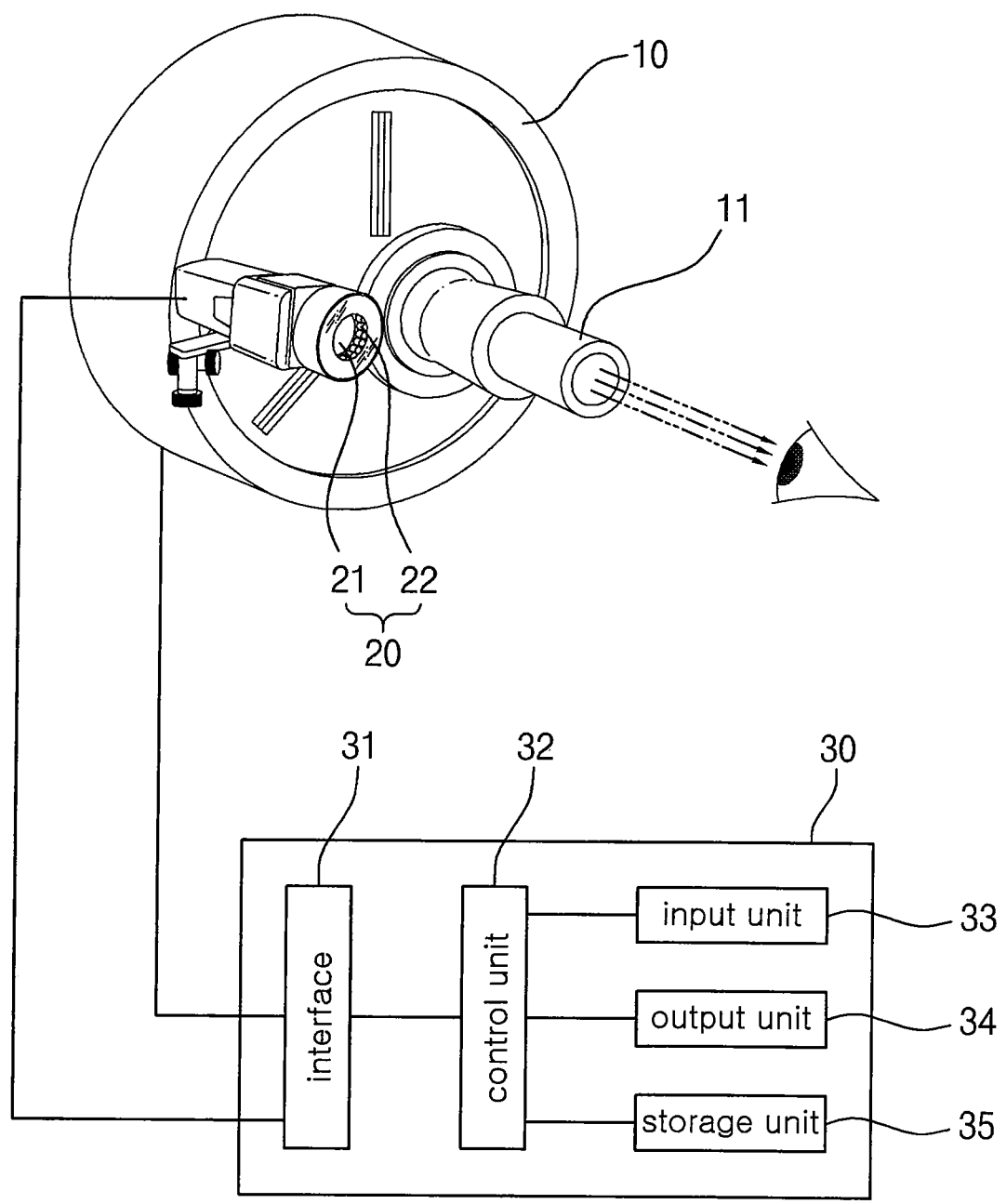
FIG. 2 is a diagram showing the construction of an embodiment of an eyeball tumor treatment system to which a method of tracking the movement of the eyeball in eyeball tumor treatment according to the present invention is applied.

FIG. 2 is a diagram showing the construction of an embodiment of an eyeball tumor treatment system to which a method of tracking the movement of the eyeball in eyeball tumor treatment according to the present invention is applied.

The present invention relates to the method of tracking the eyeball that is used in a process of treating the tumor of the eyeball using a proton beam. The most important process of the eyeball tumor treatment using a proton beam is persistently maintaining a patient's pupil (eyeball) at the location of the eyeball, set at the time of planning treatment, during actual treatment. For this purpose, in the present invention, a system is reconfigured, as shown in FIG. 2. The eyeball tumor treatment system to which the method of tracking the eyeball in eyeball tumor treatment according to the present invention is applied includes a proton beam output device 10 for outputting a proton beam so as to treat the tumor of the eyeball, a detection device 20 for detecting the movement of the eyeball under tumor treatment using the proton beam output device, and a control device 30 for analyzing information about the movement of the eyeball transmitted from the detection device and then controlling the operation of the proton beam output device depending on the movement of the eyeball.

The proton beam output device 10 is used to treat the eyeball tumor. A currently used proton beam output device is used as the proton beam output device 10, a detailed description of which is omitted here.

The detection device 20 functions to detect the movement of the eyeball under the eyeball tumor treatment. A patient's eyeball images detected by the detection device are transmitted to the control device 30. Accordingly, the detection device 20 must be disposed adjacent to the proton beam output device 10. Preferably, as shown in FIG. 2, the detection device 20 is disposed adjacent to the emission hole 11 of the proton beam output device 10 from which a proton beam is output. Meanwhile, the detection device 20 to which the present invention is applied may be constructed with a CCD camera. In particular, the diction device 20 may include a lens 21 for receiving images and infrared Light Emitting Diodes (LEDs) 22 for generating infrared rays. Since a lens that is applied to a conventional detection device has only a simple iris diaphragm adjusting function, it has a disadvantage in that it is difficult and inconvenient to adjust an actual focus. In the case where eyeball pattern matching software is employed, it is necessary to prevent the light of a fluorescent lamp and other images attributable to an environment from being formed on the pupil in order to improve accuracy. Accordingly, the detection device 20 according to the present invention eliminates ambient light and images attributable to an environment using infrared rays. To this end, it is preferable to lower illumination in a treatment room. Furthermore, the camera lens 21 applied to the detection device 20 is configured to allow the adjustment of magnification, the adjustment of a focus and the adjustment of an iris diaphragm to be remotely performed by the control device 30 in an adjustment room. The infrared LEDs 22 are disposed around the lens 21.

That is, a first characteristic of the detection device 20 to which the present invention is applied is that the infrared LEDs 22 using infrared rays that cannot be viewed by humans' eyes and can be captured by a camera are arranged adjacent to the lens 21 of the detection device in order to decrease the reduction in analytical sensitivity due to ambient light impinging on a patient's eyeball, thereby facilitating the image analysis of the control device. In other words, in order to accurately analyze a patient's eyeball image, it is important to obtain precise and high-quality patterns. In a general environment, it is difficult to acquire clear eyeball images due to various surrounding illumination devices (a fluorescent lamp, an interior illumination lamp, a computer, a camera reflection image, and the like). Therefore, in order to eliminate the above-described condition, the present invention allows infrared LEDs 22 to be installed in the detection device 20, so that necessary illumination and a uniform pattern are provided inside the eyeball, thereby assisting pattern matching.

A second characteristic of the detection device 20 is that the camera lens 21 applied to the detection device 20 is configured to allow the adjustment of magnification, the adjustment of a focus and the adjustment of an iris diaphragm to be performed by the control device 30 at a remote location. That is, although the conventional camera lens has a disadvantage in that it is difficult and inconvenient to adjust an actual focus because it has only a simple iris diaphragm adjustment function, the present invention is characterized in that the lens can be adjusted by the control device 30 in various ways.

The detection device 20 having the above-described construction transmits images received through the lens to the image acquisition board (NI Vision acquisition board) (interface) of the control device 30. The control device 30 stores and analyzes images received through the interface using a method according to the present invention, which will be described later.

The control device 30 functions to receive a template image of a patient's eyeball from the detection device 20, store the template image, receive a treatment image of the eyeball during eyeball tumor treatment, compare the treatment image with the template image, and stop the operation of the proton beam output device if the movement of the eyeball is detected. As shown in FIG. 2, the control device 30 includes an interface 31 for communicating with the proton beam output device 10 and the detection device 20 and performing an image acquisition board function that connects hardware and software with each other, an input unit 33 for receiving various types of control signals from a user, a storage unit 35 for storing various types of image information transmitted from the detection device 20 and various types of program information used to implement the method of tracking the eyeball in the eyeball tumor treatment according to the present invention, a control unit 32 for comparing a template image with a treatment image and controlling the function of the proton beam output device based on the results of the comparison, and an output unit 34 for outputting various types of information under the control of the control unit 32. Meanwhile, the images transmitted from the detection device 20 may be analyzed by the control device 30 through the image analysis program of LabView, which has been widely used in foreign countries and domestic major company laboratories in the field of automatic control measurement and which is a graphic-based program language that has been used for the development of advanced technology. That is, the present invention may be implemented in the form of an image analysis program, and may be run in the control device 30.

Figure 3:
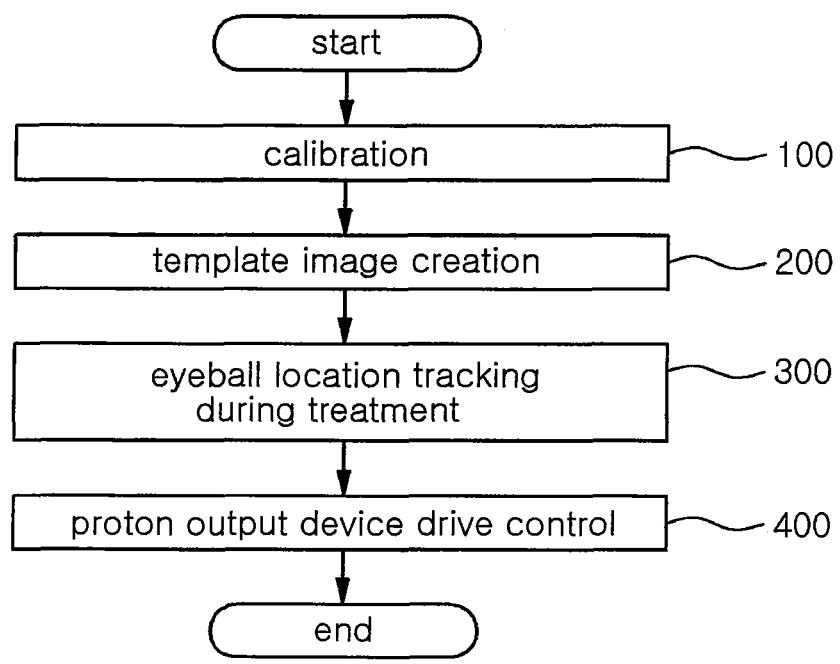
FIG. 3 is a flowchart showing an embodiment of the method of tracking the movement of the eyeball in eyeball tumor treatment according to the present invention.

FIG. 3 is a flowchart showing an embodiment of the method of tracking the movement of the eyeball in eyeball tumor treatment according to the present invention.

The method of tracking the movement of the eyeball in eyeball tumor treatment according to the present invention, as shown in FIG. 3, includes a calibration step 100 of performing various types of setting on the detection device 20, a template image generation step 200 for generating a patient's eyeball image received from the detection device 20 as a template image and storing the template image in the control device 30, an eyeball location tracking step 300 for analyzing the movement of the eyeball by comparing the template image with treatment images during eyeball tumor treatment using a proton beam, and a control step 400 for controlling the operation of the proton beam output device 10 using information obtained through the analysis at the eyeball location tracking step 300.

The calibration step 100 is a step of, in order to accurately analyze the image of the patient's eyeball, measuring the image focus of the detection device 20 and the actual distance for each pixel and storing them in the storage unit 35, and is performed before the actual initiation of eyeball tumor treatment. In the present invention, in order to prepare for unexpected situations in actual patient treatment, a mm value is determined for each pixel of an image using any one of various methods including Point Detection, Edge Detection, Line Measurement and Manual Input at the calibration step. That is, the calibration step is a step of determining an actual length to which the length of an image viewed through the display of the output unit corresponds and storing the actual length in the storage unit 35.

The template image generation step 200 is a step of generating a template image of a patient's eyeball and storing the template image in the storage unit 35, and is performed after the calibration step. That is, when in the state in which an image analysis program that is applied to the method of tracking the movement of the eyeball in eyeball tumor treatment according to the present invention is running, a patient's eyeball image is transmitted from the detection device 20 and the patient's name and RT number are input through the input unit 33, the control unit 32 matches the eyeball image to the patient's name and number and stores them in the storage unit 35 in the form of a template image.

The eyeball location tracking step 300 is a step at which during patient eyeball tumor treatment using the proton beam output device 10, the control device 32 determines whether the movement of the eyeball has occurred by comparing the template image with the treatment images of the patient's eyeball received from the detection device 20 in real time. That is, at the eyeball location tracking step 300, the control unit 32 compares and analyzes the template image and the treatment images using the mm/pixel value and the template image, which were stored at the calibration step and the template image generation step, and then outputs the location of the patient's eyeball at the time of initiation of the treatment and error through the output unit 34.

The proton beam output device operation control step 400 is a step at which the control unit 32 controls the operation of the proton beam output device 10 based on analysis results obtained at the eyeball location tracking step 300 during the treatment.

FIGS. 4 to 7 are screen shots showing various examples of screens that are used at the calibration step applied to the present invention. The calibration step will be described in detail below with reference to these diagrams.

The calibration step 100 is a step of, in order to accurately analyze an image of a patient's eyeball, measuring the image focus of the detection device 20 and the actual distance for each pixel and storing them in the storage unit 35. The control unit 30 can actually measure the distance that the eyeball has actually moved on the basis of the stored information at the eyeball location tracking step.

Figure 4:
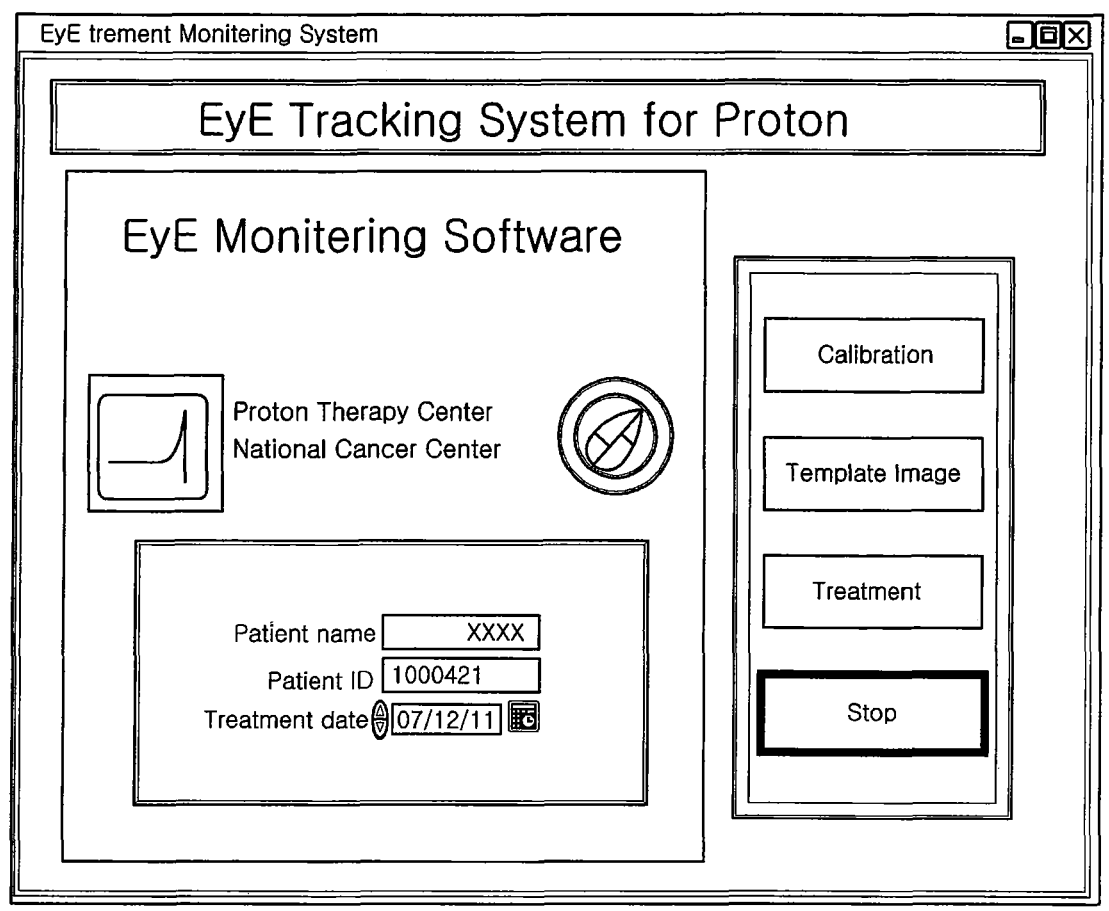
FIGS. 4 to 7 are screen shots showing various examples of screens that are used at the calibration step applied to the present invention.

When a program (hereinafter simply referred to as an 'image analysis program') for implementing the method of tracking the movement of the eyeball in eyeball tumor treatment according to the present invention is run by the control unit 32, a start window, such as that shown in FIG. 4, is activated in the output unit 34 of the control device 20. The start window includes a patient's name, patient's number and treatment date input boxes and respective function buttons. A patient's name, a patient's number and a date input through the start window and then stored are used as a file name when a patient's template image is stored later.

Figure 5:
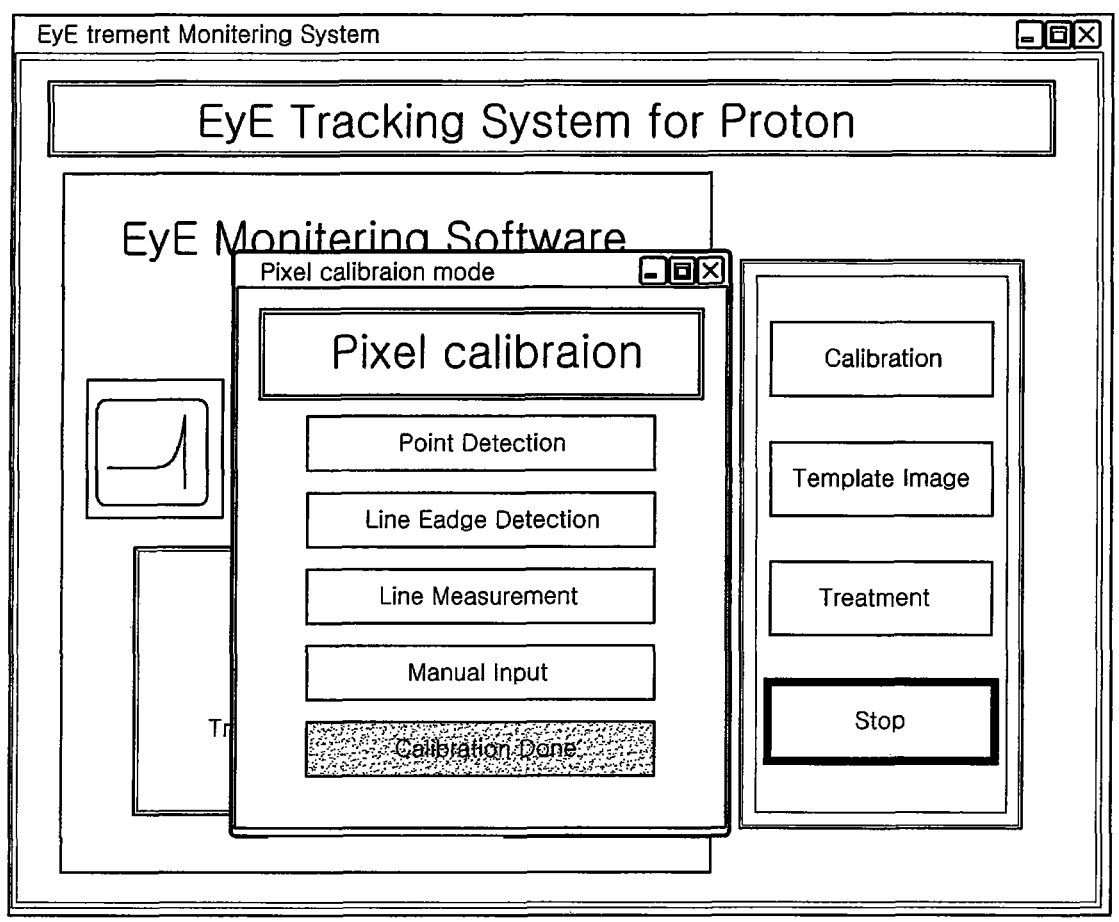

When a user selects the 'calibration' button of the start window such as that shown in FIG. 4, a new window, including four menus, including Point Detection, Edge Detection, Line Measurement and Manual Input, such as that shown in FIG. 5, is opened. Each of the functions of the four menus is used to determine a mm value for each pixel of an image. When a user encounters an unexpected situation in actual patient treatment, the user can perform the calibration step using one suitable menu selected from among the four menus. That is, the present invention proposes the four calibration methods so that the user can desirably perform the calibration step even in any unexpected situation that may occur during patient treatment.

Figure 6:
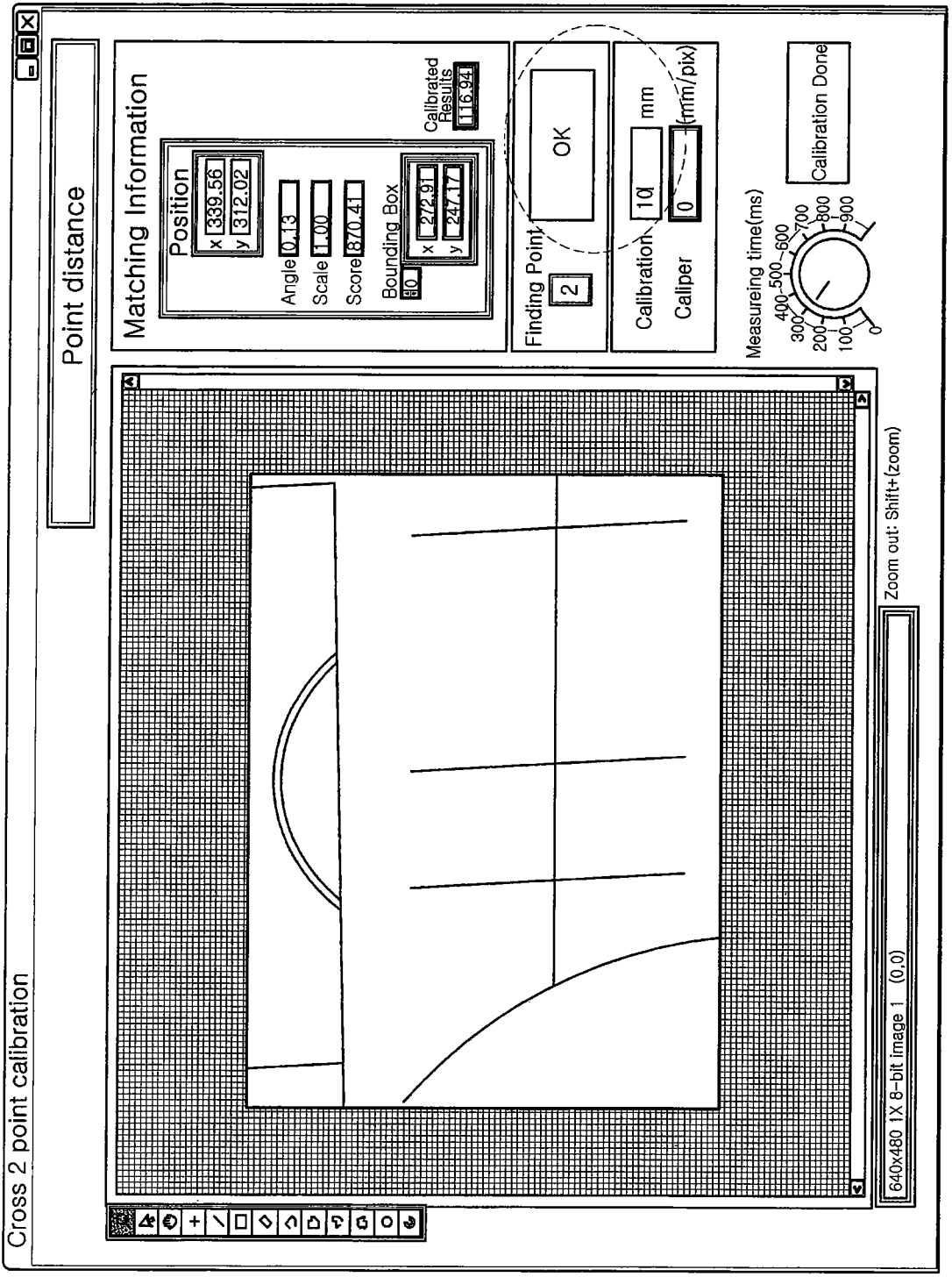

First, the first calibration method using the point detection measurement menu is described below. That is, the first calibration method is a method of automatically detecting a '+' marked standard image and measuring the number of pixels over a predetermined distance. As shown in FIG. 6, the first method is a method in which when '+' marks are respectively spaced apart by 1 cm, 2 cm and 3 cm, the control unit 30 automatically detects them and measures and stores the numbers of pixels within corresponding spaces. Here, the angles of the + marks do not matter, and the known actually measured distance between two + marks is input in millimeters. When a blue line is drawn between the two cross marks and a blue OK button is created, the calibration step is completed. That is, when a user displays two + marks at an interval of 1 mm on a white thin plastic plate so as to perform calibration, as shown in FIG. 6, and then the actually measured distance between the two cross marks is automatically detected and is input through the input unit 33, the control unit 32 calculates the distance in millimeters for each pixel using the following Equation 1 through the image analysis program.

$$\frac{\text{Calibration Value (mm)}}{\text{pixel number} - 1} = \text{mm/pixel} \qquad (1)$$

Next, the second calibration method using the line edge detection measurement menu is a method that can be effectively used when the size of a patient's eyeball is known. In general, when eyeball tumor treatment using a proton beam is planned, the geometrical information of the structure of a patient's eyeball is measured and is input to a Treatment Planning System (TPS). Accordingly, the second calibration method is a method of, in the case where the size of the pupil is accurately and actually measured through the above process, automatically detecting the boundary lines of the pupil and calculating the actual distance for each pixel through the simple drawing of a single longitudinal line by a user. That is, the second calibration method is a method in which a new still image window is opened upon input of the previously known diameter of the pupil and selection of image capture and the control unit 32 automatically extracts first and last edges along a longitudinal ROI line and calculates the distance between the edges upon drawing of the longitudinal ROI line. In this case, the locations of the start and end points of the ROI line must be present at arbitrary locations outside the edges.

Next, the third calibration method using the line profile measurement menu is basically similar to the second calibration method, but enables measurement using an arbitrary quantified object in the case where it is difficult to detect the edge of the pupil or to know the accurate size of the pupil. That is, the third calibration method enables measurement to be performed by drawing a line using an arbitrary object having a known size, such as a ruler as well as the pupil. However, when the third calibration method is used, the accurate locations of start and end points must be given unlike those in the second calibration method.

Figure 7:
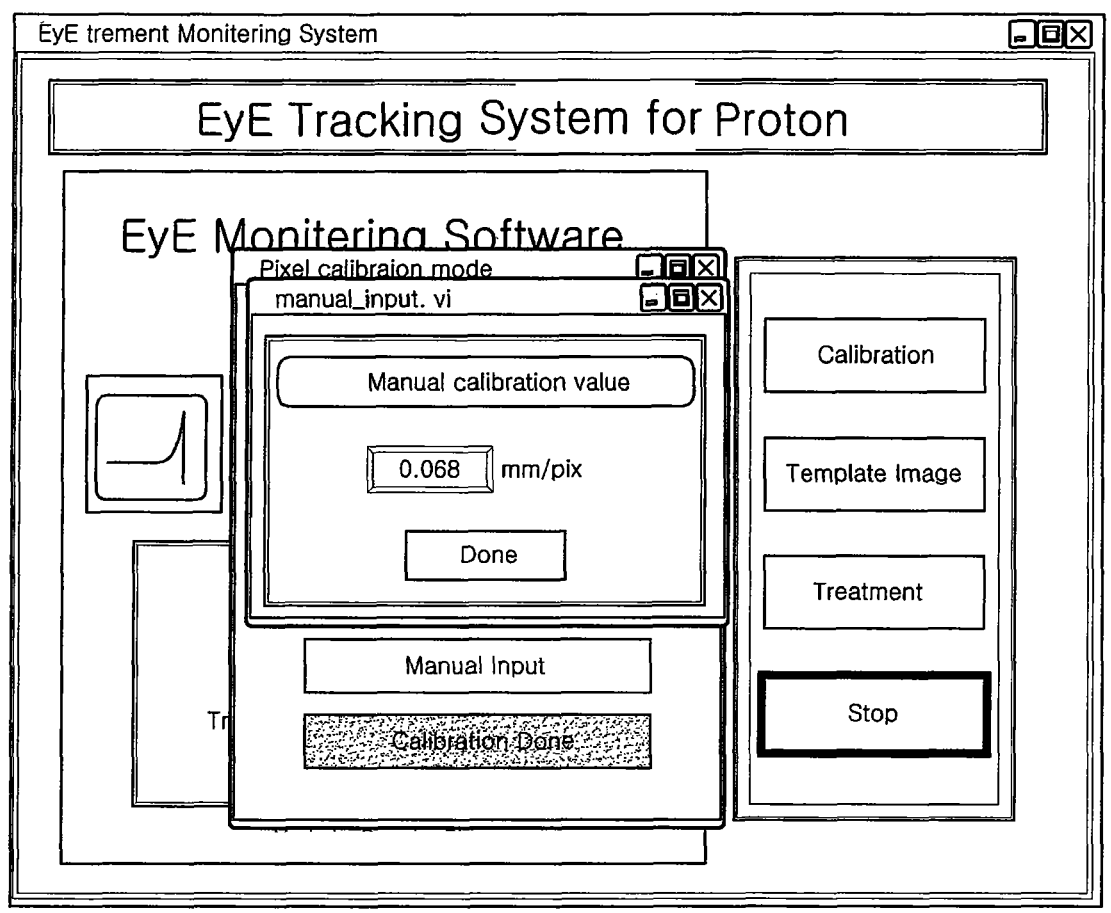

Finally, the fourth calibration method using the manual input menu is a method for inputting and using an existing calibration value without performing calibration again in the case where one or more pixel calibration processes have been performed and the existing calibration value is known, as shown in FIG. 7.

Since the error between pixel calibration values based on the above-described four methods is 0.02 mm or less and the use of any one selected from among the four methods does not greatly influence location analysis in the process of tracking the movement of the eyeball in eyeball treatment, a user may use any one of the calibration methods depending on a patient's situation or environmental conditions.

Figure 8:
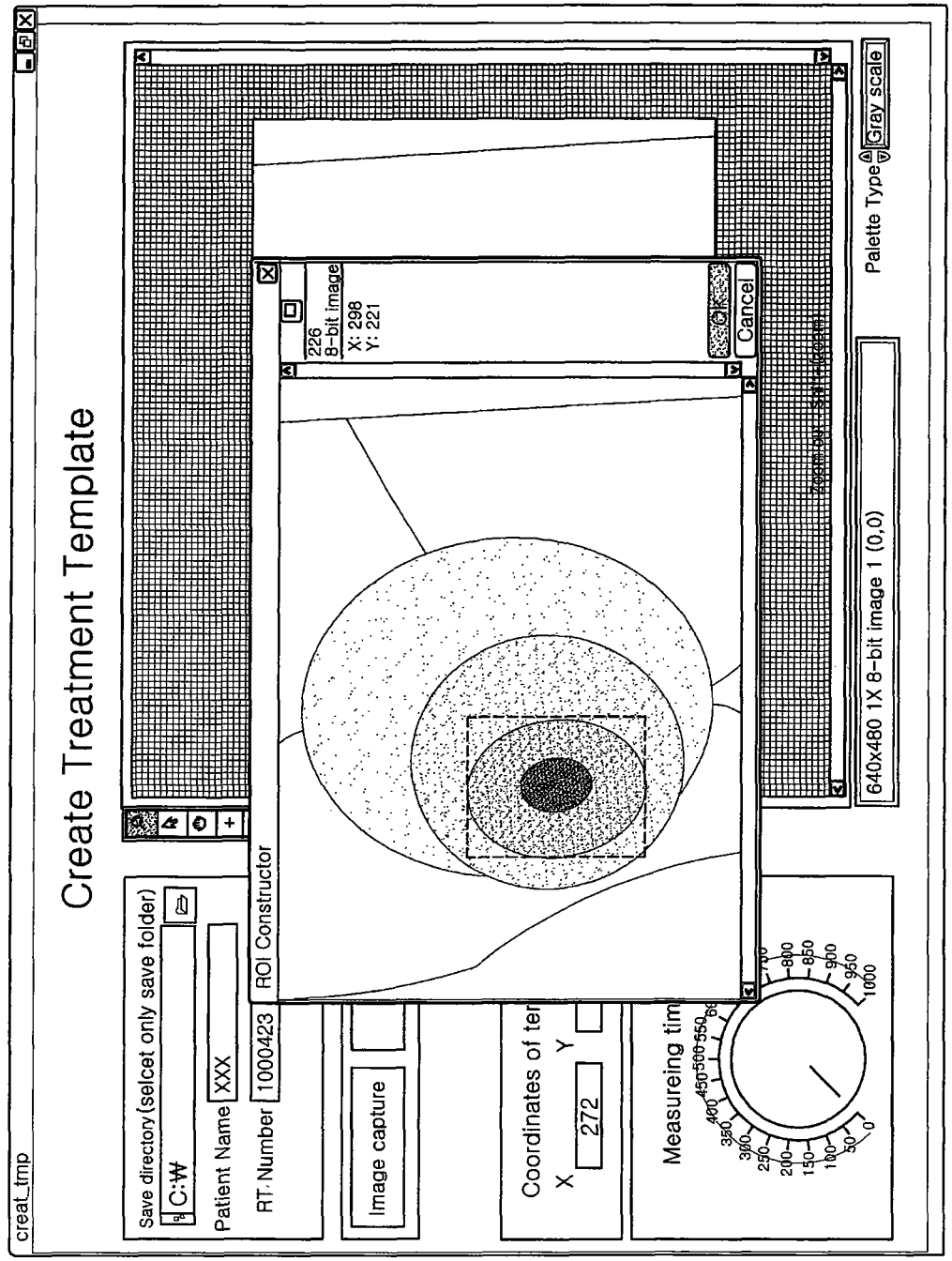
FIG. 8 is a screen shot showing an example of a screen that is used at the template image generation step applied to the present invention.

FIG. 8 is a screen shot showing an example of a screen that is used at the template image generation step applied to the present invention. The template image generation step will be described in detail with reference to this drawing.

The template image generation step 200 is a step of generating a template image of a patient's eyeball and storing it in the storage unit 35, and is performed after the calibration step. That is, when in the state in which the image analysis program is running, the patient's eyeball image is transmitted from the detection device 20 and the patient's name and RT number are input through the input unit 33, the control unit 30 matches the image to the patient's name and RT number and stores it in the storage unit 35. At this time, it is preferable to perform a step of adjusting the surrounding illumination of the detection device 20 and the iris diaphragm of the camera of the detection device 20 so as to desirably identify the patient's eyeball. That is, when a measurer locates the patient's eyeball as near to the center of the screen of the output unit 34 as possible, as shown in FIG. 8, and then presses the 'Temp Image Save' button of the image analysis program, the control unit 32 stores the template image in the storage unit in the form of a bmp file having a name identical to the patient's number recorded in the patient's RT number. When the stored bmp image is read again through the Vision Assistant program and a measurer selects a region from the image, the control unit 32 stores the selected region as the patient's eyeball template image in the storage unit 35.

In greater detail, after the calibration step has been performed, a template image of the patient's eyeball and relevant reference origin coordinates must be set during treatment based on a treatment plan. The present invention enables this process to be simply performed by storing one image and setting an ROI. FIG. 8 shows the state in which a new window for generating a template image is opened when the 'template image' button of FIG. 4 is selected. Meanwhile, a user selects a folder in which the generated template image will be stored, and performs image capture. When a still image window is created, the user designates a desired template image. It is possible to set any portion at any location. However, it is preferable to select and store a characteristic portion so as to be advantageous to the tracking of the pupil. Here, the coordinates of the center of the ROI created in the pixel 640×480 region of the entire image of the template image are recorded together, and become the basic location of the pupil required during actual treatment.

When a template image is stored, the file name of the template image is set based on the patient's name, the patient's number and the date input as shown in FIG. 4, and is stored in the form of "patientnumber_name_date.png." The name of the file may be modified by a user.

Figure 9:
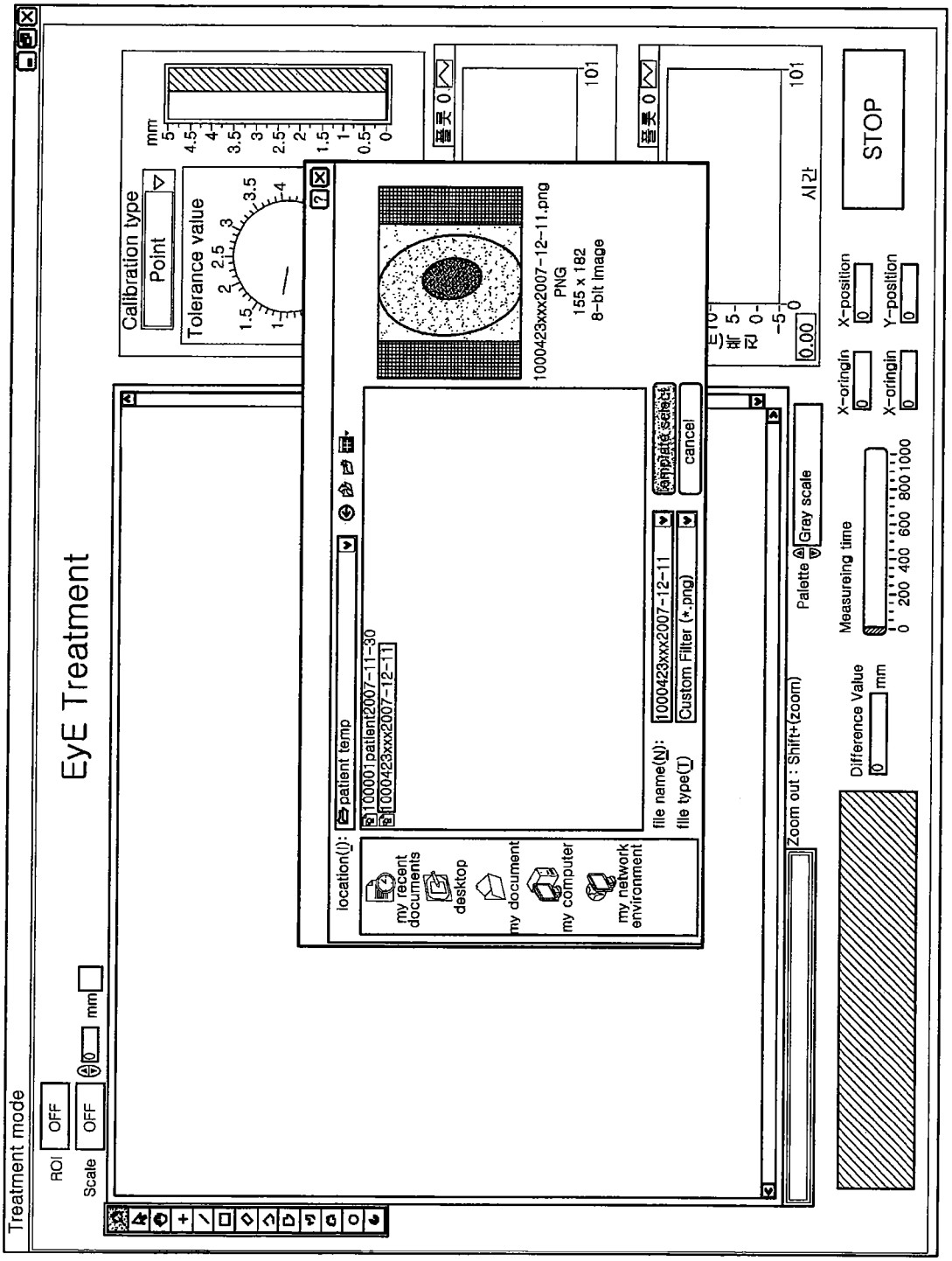
FIGS. 9 to 11 are diagrams showing examples of various screens that are used at the eyeball location tracking step applied to the present invention.
Figure 10:
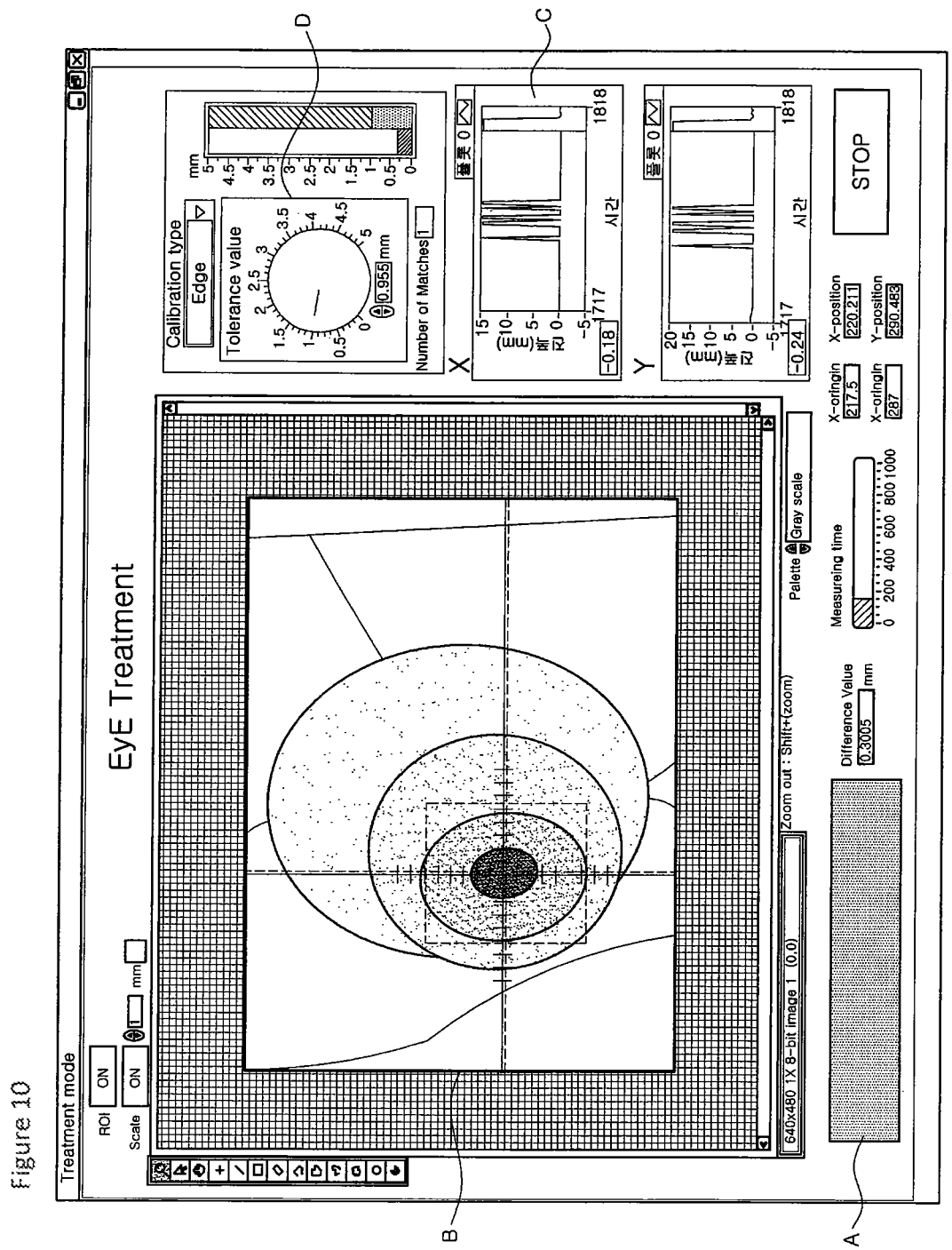
Figure 11:
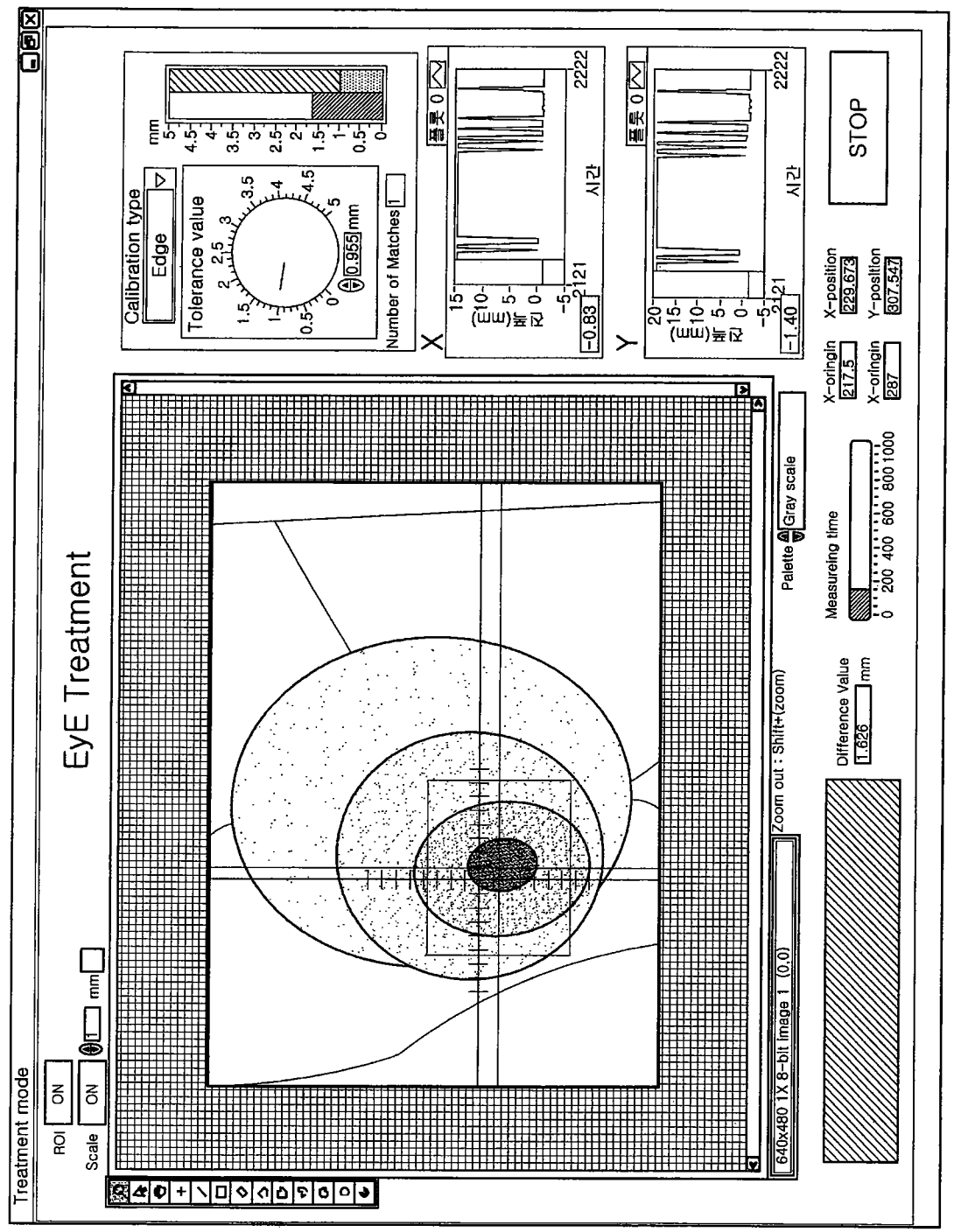

FIGS. 9 to 11 are diagrams showing examples of various screens that are used at the eyeball location tracking step applied to the present invention. The eyeball location tracking step will be described in detail below with reference to the diagrams.

The eyeball location tracking step 300 is a step at which while the patient's eyeball tumor is treated using the proton beam output device 10, the control device 30 determines whether the movement of the eyeball has occurred by receiving the patient's eyeball image from the detection device 20 in real time and comparing the patient's eyeball image with the template image. That is, at the eyeball location tracking step, the control unit 32 compares the template image with periodically acquired treatment images using the mm/pixel value and the template image stored through the calibration step and the template image generation step, thereby detecting a specific pattern set in the template image and showing a location at the start of the treatment and error.

In greater detail, the eyeball location tracking step is a step of comprehensively analyzing the movement of the eyeball using various types of information obtained at the above-described steps while actually treating the patient's eyeball tumor using a proton beam.

In the case where the template image is set as described above, the origin coordinates of the template image in the entire screen are detected and stored together. The control unit 32 determines the location of the eyeball and real-time coordinate information by comparing the set template image and the origin coordinates with the image information of the eyeball image input in real time, determines variation in location based on the template image by performing comparison with the origin coordinates, and outputs a 'pass' signal if the variation is less than or equal to a tolerance value and a 'fail' signal if the variation is greater than the tolerance value.

First, when the 'treatment' button of FIG. 4 is selected, an eyeball location tracking (eye treatment) task window is opened and a window for selecting the template image is opened also, as shown in FIG. 9. The user selects the template image, and selects the calibration method performed at the calibration step using a calibration menu. Here, if the calibration method that was not used at the calibration step is selected, the image analysis program may run abnormally. That is, the user must select a calibration method identical to the calibration method, which was actually selected from among the above-described four calibration methods at the calibration step 100, at the eyeball location tracking step 300.

Meanwhile, when the tolerance value is set in the eyeball location tracking task window, the control unit 32 generates a 'pass' signal for variation in the location of the eyeball equal to or less than the set tolerance value, thereby displaying the status display bar A of a screen in green as shown in FIG. 10, and also displaying the lines of the treatment image transmitted from the detection device 20 in green.

In contrast, when the movement of the patient's eyeball deviates from the tolerance range, the control unit 32 displays the entire screen, and the status display bar A and the lines of the treatment image in red, as shown in FIG. 11.

In greater detail, FIGS. 10 and 11 show a Graphic User Interface (GUI) at the eyeball location tracking step of the image analysis program. The GUI includes a box B for viewing a patient's image, a level box D for inputting a tolerance value that designates a tolerance range for the movement of the eyeball, a graph box C for showing the distance of deviation from a treatment location along the X and Y axes in millimeters, and a status display bar A. That is, FIG. 10 shows the case where the movement of the patient's eyeball under tumor treatment is within a tolerance range, in which case the status display bar A is displayed in green. Furthermore, the present invention allows the tolerance value for the movement of the eyeball during treatment to be variably set within a range from 0 mm to 5 mm through the level box D of the image analysis program. Meanwhile, in the present invention, the control unit 32 displays the status display bar A under the image view box B in green as shown in FIG. 10 when the location of the eyeball in the treatment image exists within the tolerance range. In contrast, the control unit 32 displays the status display bar A in red, thereby issuing an alarm, as shown in FIG. 11, when the location of the eyeball in the treatment image deviates from the treatment tolerance range or there is no pattern of a template image that matches the treatment image. As the results of simulations related to the present invention, the tracking of a patient's eyeball could restrict the movement of the eyeball within an average of 1 mm and the movement of the eyeball could be detected at a resolution of 0.03 mm. However, the present invention is not limited thereto. That is, the control unit 32 can not only issue an alarm indicative of the deviation of the movement of the eyeball from the tolerance range by varying the color of the status display bar A, but can also output an alarm message through the speaker of the output unit 34.

Meanwhile, at the eyeball location tracking step 300, the control unit 32, in the case where it needs to display the status display bar A in red, stops the operation of the proton beam output device 10, thereby preventing a proton beam from being radiated onto the patient's eyeball at step 400. That is, this case implies that the location of the treatment image deviates from the tolerance range on the basis of the location of the template image. In this case, the patient's eyeball may be fatally damaged by the proton beam, so that the control unit 32 calls a user's attention by switching the status display bar A to a red color, and shuts off the output of a proton beam by instantaneously stopping the operation of the proton beam output device 10.

However, in the case where the location of the treatment image is determined to exist within the tolerance range on the basis of the location of the template image, the control unit 32 performs a control operation so that the status display bar A can not only be displayed in green but a proton beam can be also normally operated.

The present invention has an advantage in that it is capable of blocking the output of a proton beam when the range of movement of the eyeball is greater than a preset tolerance value during eyeball tumor treatment using the proton beam, thereby preventing the side effect of the proton beam on the eyeball.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of tracking movement of an eyeball in eyeball tumor treatment, the method being applied to an eyeball tumor treatment system, the method comprising:
    a calibration step of a control unit of a control device of the eyeball tumor treatment system storing an actual length for each pixel of an image, output through an output unit of the control device, in a storage unit of the control device, wherein the calibration step comprises:
    automatically detecting a '+' marked standard image and measuring the number of pixels over a predetermined distance; automatically detecting the boundary lines of the pupil and calculating the actual distance for each pixel through the drawing of a single longitudinal line;
    drawing a line using an arbitrary object having a known size as well as the pupil;
    a template image generation step of the control unit storing a patient's eyeball image, transmitted from the detection device of the eyeball tumor treatment system, as a template image of the patient's eyeball in the storage unit;
    an eyeball location tracking step of, during treatment of the patient's eyeball using a proton beam output device of the eyeball tumor treatment system, the control unit determining whether movement of the treatment image has occurred by comparing treatment images of the patient's eyeball received from the detection device in real time with the template image; and
    a control step of the control unit stopping operation of the proton beam output device if, as a result of the determination, the movement of the treatment image is determined to deviate from a preset tolerance range, and keeping operation of the proton beam output device normal if, as a result the determination, the movement of the treatment image range is determined to be within the tolerance range.

2. The method as set forth in claim 1, wherein the eyeball location tracking step is performed in such a way that the control unit determines a range of the movement of the treatment image using center coordinates of the template image and the distance for each pixel, which have been stored at the calibration step.

3. The method as set forth in claim 1, wherein the eyeball location tracking step is performed in such a way that the control unit compares treatment images captured by infrared Light Emitting Diodes (LEDs) of the detection device with the template image.

4. The method as set forth in claim 3, wherein operation of a lens of the detection device or the infrared LEDs is controlled by the control device.

5. The method as set forth in claim 1, wherein the control step comprises the control unit outputting an alarm message through the output unit if the movement of the treatment image is determined to deviate from the preset tolerance range.

* * * * *